United States Patent
McCarthy

(10) Patent No.: US 11,253,287 B2
(45) Date of Patent: Feb. 22, 2022

(54) RETROGRADE BLOOD FLOW OCCLUSION FLUSHING DEVICE

(71) Applicant: Neuravi Limited, Galway (IE)

(72) Inventor: Ray McCarthy, Galway (IE)

(73) Assignee: NEURAVI LIMITED, Galway (IE)

( * ) Notice: Subject to any disclaimer, the term of this patent is extended or adjusted under 35 U.S.C. 154(b) by 442 days.

(21) Appl. No.: 16/152,159

(22) Filed: Oct. 4, 2018

(65) Prior Publication Data

US 2020/0107851 A1    Apr. 9, 2020

(51) Int. Cl.
*A61B 17/3203*   (2006.01)
*A61B 17/12*   (2006.01)
(Continued)

(52) U.S. Cl.
CPC .... *A61B 17/32037* (2013.01); *A61B 17/1204* (2013.01); *A61B 17/12109* (2013.01);
(Continued)

(58) Field of Classification Search
CPC .......... A61B 17/32027; A61B 17/1204; A61B 17/12109; A61B 17/12136; A61B 17/22031; A61B 2017/22038; A61B 2017/22094; A61B 2217/007; A61B 17/12168; A61B 17/221; A61B 2017/22051; A61B 2017/22034; A61B 2017/22035; A61B 17/22; A61B 2017/22067; A61B 17/32037;
(Continued)

(56) References Cited

U.S. PATENT DOCUMENTS

| 5,928,192 A | 7/1999 | Maahs |
| 6,080,170 A | 6/2000 | Nash et al. |

(Continued)

FOREIGN PATENT DOCUMENTS

| WO | 00/54673 | 9/2000 |
| WO | 2013/105099 | 7/2013 |
| WO | 2014/204860 | 12/2014 |

OTHER PUBLICATIONS

Sorimachi et al., "Blood pressure measurement in the artery proximal and distal to an intra-arterial embolus during throbolytic therapy", J. NeuroInterventional Surgery, vol. 3, Issue 1 (Dec. 16, 2010), pp. 43-46.

(Continued)

*Primary Examiner* — Kevin C Sirmons
*Assistant Examiner* — Alexandra Lalonde
(74) *Attorney, Agent, or Firm* — Cohen & Hildebrand, PLLC

(57) ABSTRACT

A device and method for establishing retrograde blood flow during recanalization of a vessel having a targeted blockage. While in a collapsed state an occluding component is introduced distally intravascularly traversing the targeted blockage to its distal side. Then, the occluding component transitions to an expanded state having an enlarged diameter forming a seal with an internal wall of the vessel prohibiting anterograde blood flow beyond the expanded occluding component. Retrograde blood flow is thereby established in a region of the vessel bound at one end by the occluding component and at an opposite end by the targeted blockage by dispensing a flushing fluid into the region of the vessel.

20 Claims, 7 Drawing Sheets

(51) Int. Cl.
*A61B 17/22* (2006.01)
*A61M 25/00* (2006.01)
*A61M 25/10* (2013.01)

(52) U.S. Cl.
CPC .. *A61B 17/12136* (2013.01); *A61B 17/22031* (2013.01); *A61B 2017/22038* (2013.01); *A61B 2017/22094* (2013.01); *A61B 2217/007* (2013.01); *A61M 25/0026* (2013.01); *A61M 2025/1061* (2013.01)

(58) Field of Classification Search
CPC ........ A61B 17/12022; A61B 17/12027; A61B 17/12113; A61B 17/12118; A61B 17/3486; A61B 17/22048; A61M 25/0026; A61M 2025/1061; A61M 2025/0681; A61M 25/0662; A61M 25/003; A61M 31/005; A61M 25/104; A61M 2025/1052; A61M 25/10; A61M 2025/1043; A61M 2025/1045
See application file for complete search history.

(56) References Cited

U.S. PATENT DOCUMENTS

| | | | |
|---|---|---|---|
| 6,168,579 B1 | 1/2001 | Tsugita | |
| 6,196,994 B1 | 3/2001 | Maahs | |
| 6,620,148 B1 | 9/2003 | Tsugita | |
| 6,635,070 B2 | 10/2003 | Leeflang et al. | |
| 6,994,718 B2 | 2/2006 | Groothuis et al. | |
| 7,981,129 B2 | 7/2011 | Nash et al. | |
| 8,226,673 B2 | 7/2012 | Nash et al. | |
| 8,444,665 B2 | 5/2013 | Tsugita | |
| 9,084,857 B2 | 7/2015 | Cully et al. | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign et al. | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman et al. | |
| 9,770,577 B2 | 9/2017 | Li et al. | |
| 9,775,621 B2 | 10/2017 | Tompkins et al. | |
| 9,775,706 B2 | 10/2017 | Peterson et al. | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman et al. | |
| 9,833,252 B2 | 12/2017 | Sepetka et al. | |
| 9,833,604 B2 | 12/2017 | Lam et al. | |
| 9,833,625 B2 | 12/2017 | Waldhauser et al. | |
| 2002/0032432 A1 | 3/2002 | Nash et al. | |
| 2002/0169436 A1 | 11/2002 | Gurm et al. | |
| 2004/0054347 A1* | 3/2004 | Zadno-Azizi | A61B 17/22 604/509 |
| 2005/0085769 A1 | 4/2005 | MacMahon et al. | |
| 2005/0113798 A1 | 5/2005 | Slater et al. | |
| 2010/0069900 A1* | 3/2010 | Shirley | A61M 25/104 606/21 |
| 2013/0158511 A1 | 6/2013 | Aggerholm | |
| 2016/0338720 A1 | 11/2016 | Kassab et al. | |
| 2017/0007264 A1 | 1/2017 | Cruise et al. | |
| 2017/0007265 A1 | 1/2017 | Guo et al. | |
| 2017/0020670 A1 | 1/2017 | Murray et al. | |
| 2017/0020700 A1 | 1/2017 | Bienvenu et al. | |
| 2017/0027640 A1 | 2/2017 | Kunis et al. | |
| 2017/0027692 A1 | 2/2017 | Bonhoeffer et al. | |
| 2017/0027725 A1 | 2/2017 | Argentine | |
| 2017/0035436 A1 | 2/2017 | Morita | |
| 2017/0035567 A1 | 2/2017 | Duffy | |
| 2017/0042548 A1 | 2/2017 | Lam | |
| 2017/0049596 A1 | 2/2017 | Schabert | |
| 2017/0071737 A1 | 3/2017 | Kelley | |
| 2017/0072452 A1 | 3/2017 | Monetti et al. | |
| 2017/0079671 A1* | 3/2017 | Morero | A61M 25/0194 |
| 2017/0079680 A1 | 3/2017 | Bowman | |
| 2017/0079766 A1 | 3/2017 | Wang et al. | |
| 2017/0079767 A1 | 3/2017 | Leon-Yip | |
| 2017/0079812 A1 | 3/2017 | Lam et al. | |
| 2017/0079817 A1 | 3/2017 | Sepetka et al. | |
| 2017/0079819 A1 | 3/2017 | Pung et al. | |
| 2017/0079820 A1 | 3/2017 | Lam et al. | |
| 2017/0086851 A1 | 3/2017 | Wallace et al. | |
| 2017/0086996 A1 | 3/2017 | Peterson et al. | |
| 2017/0095259 A1 | 4/2017 | Tompkins et al. | |
| 2017/0100126 A1 | 4/2017 | Bowman et al. | |
| 2017/0100141 A1 | 4/2017 | Morero et al. | |
| 2017/0100143 A1 | 4/2017 | Grandfield | |
| 2017/0100183 A1 | 4/2017 | Iaizzo et al. | |
| 2017/0113023 A1 | 4/2017 | Steingisser et al. | |
| 2017/0147765 A1 | 5/2017 | Mehta | |
| 2017/0151032 A1 | 6/2017 | Loisel | |
| 2017/0165062 A1 | 6/2017 | Rothstein | |
| 2017/0165065 A1 | 6/2017 | Rothstein et al. | |
| 2017/0165454 A1 | 6/2017 | Tuohy et al. | |
| 2017/0172581 A1 | 6/2017 | Bose et al. | |
| 2017/0172766 A1 | 6/2017 | Vong et al. | |
| 2017/0172772 A1 | 6/2017 | Khenansho | |
| 2017/0189033 A1 | 7/2017 | Sepetka et al. | |
| 2017/0189035 A1 | 7/2017 | Porter | |
| 2017/0215902 A1 | 8/2017 | Leynov et al. | |
| 2017/0216484 A1 | 8/2017 | Cruise et al. | |
| 2017/0224350 A1 | 8/2017 | Shimizu et al. | |
| 2017/0224355 A1 | 8/2017 | Bowman et al. | |
| 2017/0224467 A1 | 8/2017 | Piccagli et al. | |
| 2017/0224511 A1 | 8/2017 | Dwork et al. | |
| 2017/0224953 A1 | 8/2017 | Tran et al. | |
| 2017/0231749 A1 | 8/2017 | Perkins et al. | |
| 2017/0252064 A1 | 9/2017 | Staunton | |
| 2017/0265983 A1 | 9/2017 | Lam et al. | |
| 2017/0281192 A1 | 10/2017 | Tieu et al. | |
| 2017/0281331 A1 | 10/2017 | Perkins et al. | |
| 2017/0281344 A1 | 10/2017 | Costello | |
| 2017/0281909 A1 | 10/2017 | Northrop et al. | |
| 2017/0281912 A1 | 10/2017 | Melder et al. | |
| 2017/0290593 A1 | 10/2017 | Cruise et al. | |
| 2017/0290654 A1 | 10/2017 | Sethna | |

(56) References Cited

U.S. PATENT DOCUMENTS

| | | |
|---|---|---|
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |

OTHER PUBLICATIONS

EP search Report for counterpart EP Application No. EP 21 16 1554 (dated Jun. 17, 2021)(pp. 10).

* cited by examiner

RETROGRADE BLOOD FLOW OCCLUSION FLUSHING DEVICE

BACKGROUND OF THE INVENTION

Field of the Invention

The present invention relates to an endovascular medical system. In particular, the present invention is directed to an improved procedure and treatment of acute ischemic stroke using a retrograde blood flow occlusion flushing device.

Description of Related Art

Acute ischemic stroke is caused by a thrombotic or embolic occlusion (e.g., blockage) in a cerebral artery of the brain. The occlusion is typically caused by a blood clot liberated from another part of the body which travels in an anterograde direction (in the direction of normal blood flow) through the vessel and eventually becomes lodged in the cerebral artery of the brain. Clots are subject to a pulsatile pressure gradient (i.e., systemic blood pressure acting on the proximal thrombus face minus the pressure from retrograde collateral blood flow at the distal thrombus face) which may compact and further wedge in place the clot within the vessel over time. In addition, some degree of biological adhesion may occur between the clot and the interior wall of the vessel.

A procedure known as a thrombectomy may be used to remove the thrombus, occlusion, blockage or clot lodged in the vessel using a mechanical device. Thrombectomy treatment or procedure is typically performed on patients within a relative short period of time following a stroke (e.g., less than an approximately 48-hour period after the occurrence of a stroke) and is best suited for large vessel occlusions typically with a diameter greater than approximately 1.0 mm. Non-invasive imaging, for example, non-contrast CT (NCCT), is typically used to determine the clot size to determine if thrombectomy treatment is suitable for that particular patient.

Thrombectomy is typically carried out using a stent-retriever style device that is attached to the end of a wire or using an aspiration catheter consisting of an open-ended tube through which suction can be applied. Often a combination of both devices is used in the same procedure. Stent-retrievers act by deploying a device over the clot, thereby engaging the clot in a meshwork of metal struts with open cells between. The clot, once engaged with the stent-retriever, is pulled from the blood vessel into a catheter. On the other hand, thrombectomy by aspiration catheter alone involves placing an aspiration catheter against the proximal face of the clot, then by applying suction using a syringe or pump the clot is sucked into the catheter. Often, simultaneous aspiration is used when employing a stent-retriever, which acts to capture any clot debris that may be produced during the mechanical extraction.

During the thrombectomy procedure or treatment a physician or interventionalist endovascularly introduces a guide catheter through the vasculature, typically in an artery located in the groin. The tip of the guide catheter is usually positioned in an extracranial vessel and acts as support for other devices during the procedure. Secondarily, the guide catheter may be used to aspirate clot and blood during the procedure. Aspiration of blood during the procedure can be used to cause flow reversal, thereby acting to reduce the potential of clot debris being flushed into distal vessels. Some guide catheters come equipped with a balloon at their distal tip, which, once inflated, the balloon ceases blood flow through the vessel and creates a better seal to facilitate flow reversal once aspiration is applied to the catheter.

During thrombectomy procedures or treatments a physician or interventionalist endovascularly introduces a guidewire through the vasculature, typically in an artery located in the groin or by direct access through the carotid artery. The guidewire is advanced through the vasculature to a location facing a proximal side of the targeted clot, blockage or occlusion. Once the guidewire is properly positioned, a microcatheter with an outer diameter typically less than approximately 1.0 mm, tracks over the guidewire passing through a lumen defined axially through the microcatheter.

The guide wire may then be advanced through the occlusion, typically the distal end of the wire is manipulated so that it is directed backwards down the vessel from which it was advanced, thereby creating a leading edge consisting of a loop. It is believed that crossing the clot with a looped wire reduces the potential for trauma to the vessel. Some physicians or interventionalists prefer to advance only the microcatheter across, around or over the clot, while retaining the guidewire distal end or tip within the lumen of the microcatheter on a proximal side facing the clot. That is, the distal end or tip of the guidewire never crosses over or around the clot to its distal side. The rationale being that the relatively soft and relatively flexible distal end of the microcatheter is less traumatic to the vasculature tissue than that of the guidewire. In many cases, due to its flexibility, it is very difficult to advance the microcatheter across, around or over the clot without the aid of the guidewire. To overcome such difficulty, the microcatheter and guidewire may be advanced across the clot together with the distal end or tip of the guidewire positioned inside the distal section of the microcatheter. Otherwise, the guidewire may be advanced forward across the clot first and then followed by the microcatheter.

During thrombectomy that involves a stent-retriever, once the micro-catheter is positioned across the clot, the guidewire is removed and replaced with the stent-retriever. The microcatheter is then withdrawn to a position proximal to the clot to enable deployment of the stent-retriever across the clot. Following this the stent-retriever is withdrawn carrying the clot embedded or engaged therein it. Often, a distal access catheter is used in combination with the stent-retriever to provide additional support in the vasculature and to enable local co-aspiration to aid in the capture of the clot. Concomitant aspiration through the distal access catheter and guide catheter is a common strategy applied also. Other times the stent-retriever is withdrawn directly into the guide catheter without the use of an intermediate distal access catheter, co-aspiration through the guide catheter is often used in this situation.

During thrombectomy that involves aspiration only, once the clot has been accessed with a wire and microcatheter, a distal access catheter is advanced to the proximal face of the clot, then the guidewire and microcatheter are removed to ensure the largest open lumen possible. Aspiration is applied to the distal access catheter using a syringe or a pump to suck the clot from the vessel. The clot sometimes blocks the end of the distal access catheter, in this situation the aspiration is maintained while the distal access catheter is withdrawn into the guide catheter with the clot captured at the end. Concomitant aspiration through the distal access catheter and guide catheter is commonly employed.

Some clots, occlusions or blockages are difficult, if not impossible, to remove using conventional mechanical thrombectomy for the treatment of acute ischemic stroke. In such occurrences it is common for the physician or interventionalist to conduct multiple attempts or passes to achieve a successful reperfusion. Undesirably, multiple attempts or passes of the mechanical thrombectomy device (e.g., stent-retriever) may result in compression, shearing and/or fragmentation (in whole or in parts) of the embolus. The probability of successful reperfusion, i.e., restoration of the flow of blood through the previously occluded vessel, may therefore be significantly reduced.

The present invention overcomes the aforementioned problems associated with conventional mechanical thrombectomy systems.

SUMMARY OF THE INVENTION

An aspect of the present invention is directed to an improved system and treatment for recanalization of blood flow through a vessel having a clot, embolus, blockage or occlusion lodged therein with minimal risk of unwanted compression, shearing and/or distal fragmentation.

Another aspect of the present invention is directed to a retrograde blood flow occlusion flushing device that establishes a reverse pressure differential wherein the pressure on the distal side of the targeted blockage is significantly greater than the pressure on the proximal side of the targeted blockage. As a result of this change in pressure differential the targeted blockage is pushed in the retrograde direction toward an aspirator catheter where it may be aspirated directly and/or captured using a mechanical removal device (e.g., stent-retriever).

Still another aspect of the present invention relates to a retrograde blood flow occlusion flushing device including a catheter body having a proximal end and an opposite distal end; at least one lumen defined longitudinally in the catheter body. The retrograde blood flow occlusion flushing device also having an occluding component disposed proximate the distal end of the catheter body and extending radially outward from the catheter body; the occluding component activatable to transition from a collapsed state to an expanded state. The occluding component having an enlarged diameter in the expanded state relative to that while in the collapsed state as measured from a longitudinal axis of the catheter body. A flushing fluid is deliverable through at least one lumen of the catheter body and exiting from a port defined in the catheter body; the port being disposed proximally of the occluding component.

Yet another aspect of the present invention is directed to a method for using a retrograde blood flow occlusion flushing device during recanalization of a vessel having a targeted blockage disposed therein, the device has been described in the preceding paragraph. Such method of use includes, while the occluding component is in the collapsed state, introducing the retrograde blood flow occlusion flushing device distally intravascularly traversing the targeted blockage until the occluding component is disposed distally of the targeted blockage. Once properly positioned distally of the targeted blockage, the occluding component is activated to transition from the collapsed state to the expanded state. While in the expanded state the enlarged diameter forming a seal with an internal wall of the vessel prohibiting anterograde blood flow distally beyond the occluding component. Thereafter, retrograde blood flow is established in a region of the vessel bound at one end by the expanded occluding component and at an opposite end by the targeted blockage by dispensing the flushing fluid from the port of the catheter body into the region of the vessel.

BRIEF DESCRIPTION OF THE DRAWING

The foregoing and other features of the present invention will be more readily apparent from the following detailed description and drawings illustrative of the invention wherein like reference numbers refer to similar elements throughout the several views and in which.

DETAILED DESCRIPTION OF THE INVENTION

The terms "distal" or "proximal" are used in the following description with respect to a position or direction relative to the treating physician or medical interventionalist. "Distal" or "distally" are a position distant from or in a direction away from the physician or interventionalist. "Proximal" or "proximally" or "proximate" are a position near or in a direction toward the physician or medical interventionist. The terms "occlusion", "clot" or "blockage" are used interchangeably.

Figure 1:
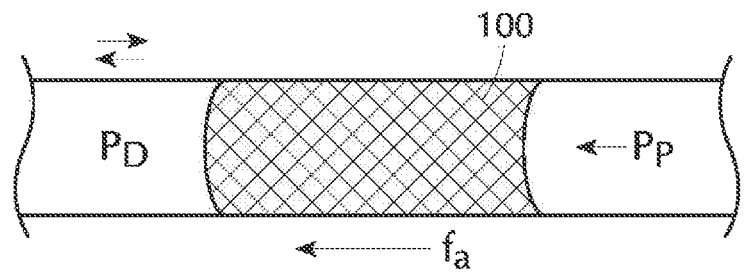
FIG. 1 is a cross-sectional view of an exemplary representation of the blood pressure in a portion of a vessel in both distal and proximal vessel segments surrounding a targeted blockage.

FIG. 1 is an exemplary illustration of a blood pressure environment of a blockage in the distal and proximal vessel segments or a portion of a vessel. A normal direction of blood flow or circulation is represented by an arrow (fa), hereinafter referred to as anterograde blood flow. Blood pressure (Pp) represents the pressure on the proximal side or face of a blockage 100, while a blood pressure (Pd) represents the pressure on the opposite distal side or face of the blockage 100. The blood pressure on the distal side (Pd) is substantially lower than the pressure on the proximal side (Pp) representing a substantial pressure differential (ΔP=Pp−Pd) that depends on such factors as the quality of blood flow through collateral blood vessels and systemic blood pressure. By way of example, T. Sorimachi, in the Journal of NeuroInterventional Surgery, Vol. 3, Issue 1 (2010) measured the mean proximal pressure as 95.2 mmHg and distal pressure at 35.9 mmHg, with the pressure differential (ΔP=Pp−Pd) being approximately 60 mmHg. This substantial pressure differential (ΔP) ensures that the blockage moves anterograde and remains lodged in tapering vessels, unless able to be overcome via mechanical intervention with an aspiration catheter or mechanically captured and extracted using an occlusion removal device such as a stent-retriever.

Figure 2A:
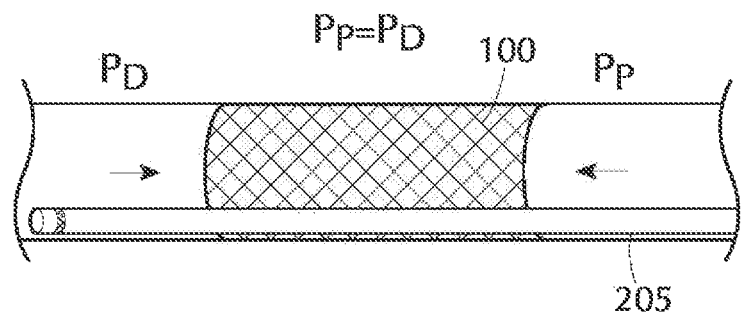
FIG. 2A is a cross-sectional view of the portion of the vessel including the targeted blockage in FIG. 1 traversed by a microcatheter during a thrombectomy procedure, wherein during traversal of the blockage an opening or patent channel is formed that allows blood flow to freely traverse the blockage wherein the pressure on the proximal and distal sides of the blockage is equalized.
Figure 2B:
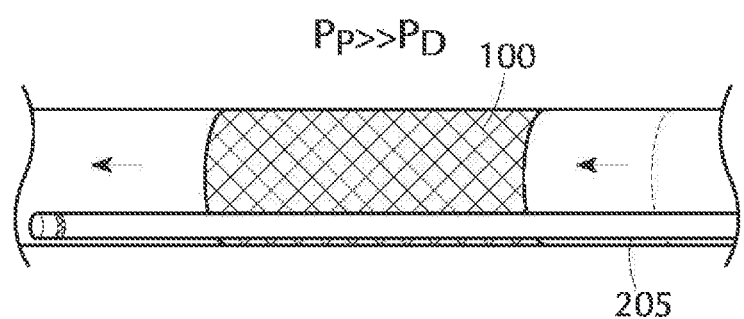
FIG. 2B is a cross-sectional view of the portion of the vessel including the targeted blockage in FIG. 1 traversed by a microcatheter during a thrombectomy procedure, wherein during traversal of the blockage either: (i) a seal is formed about the microcatheter so that the pressure differential on the distal and proximal sides of the blockage remains unchanged; or (ii) a relatively small amount of blood flow is allowed to traverse the blockage, but insufficient to reverse or even equalize the pressure differential on the distal and proximal sides of the blockage.

During some thrombectomy procedures, traversal of a blockage by a guidewire and/or microcatheter may affect the pressure differential (ΔP). FIGS. 2A and 2B illustrate two exemplary effects on the pressure differential (ΔP) when the blockage 100 is traversed by a microcatheter 205. Of course, similar principles are equally applicable if the blockage is traversed by a guidewire, instead of a microcatheter, or if the blockage is traversed using both components simultaneously. One way the pressure differential may be affected is depicted in the exemplary illustration of FIG. 2A in which the seal between the blockage 100 and the inner surface of the vessel wall is broken by the passage of the microcatheter 205 from the proximal side to the opposite distal side of the blockage. The guidewire and/or microcatheter when traversing the blockage creates a patent opening or channel extending from the proximal side to its opposite distal side/face. Such opening or patent channel may be created between the blockage and the inner wall of the vessel, or through at least a portion of the blockage itself. Since the opening or patent channel allows unobstructed and free flow of blood therethrough the pressure differential (ΔP) is equalized (Pp=Pd).

At other times, traversal of the blockage 100 by the microcatheter 205 may result in the pressure differential (ΔP) remaining substantially unchanged, as illustrated in FIG. 2B. This may occur if the blockage 100 forms a seal about the microcatheter 205 while traversing the blockage, whereby no blood flow is permitted to traverse the blockage. Otherwise, a small amount of blood flow may traverse from the proximal to the distal side of the blockage (e.g., Factional Flow Reserve<approximately 0.5), however, not sufficient to equalize the pressure differential (ΔP) so the pressure differential remains substantially unchanged (Pp>>Pd). When traversing the blockage with the microcatheter 205 in FIG. 2B the blockage 100 may undesirably move or advance in a distal direction in the vessel.

The present invention is employed during a revascularization procedure or treatment for establishing retrograde blood flow (reversal of blow flow opposite normal directional flow) by intentionally establishing a reverse pressure differential (ΔP) across the blockage, that is, the pressure on the distal side of the blockage (Pd) is increased until substantially greater than that of the pressure on the proximal side of the blockage (Pp){e.g., (Pd>>Pp)}. As a result, the blockage is advantageously pushed in a retrograde direction of blood flow (opposite normal blood flow direction, e.g., anterograde direction) proximally through the vessel. Initially, the pressure differential is sufficiently large to dislodge the targeted blockage abutted to the inner walls of the vessel. Once dislodged, thereafter the pressure differential may be reduced, but still be sufficient to propel the blockage proximally through the vessel. By way of illustrative example, initially the pressure may be increased on the distal face of the of the targeted blockage until the pressure differential is at least approximately 25%, thereafter the pressure differential may be reduced in value to at least approximately 5%.

Retrograde (reversal relative to that of normal) of blood flow is achieved in accordance with the present invention by positioning distal to a targeted blockage a retrograde (reversal) blood flow occlusion flushing device including a catheter body with an occluding component disposed proximate a distal end of the catheter body. The occluding component upon activation transitions from an unsealed, unblocked, collapsed or deflated state to a sealed, blocked, occluded, extended or inflated state. In the extended or inflated state (having a larger diameter), the occluding component flares radially outward as measured from the longitudinal axis of the catheter body farther in comparison to that while in a deflated or compressed state (having a reduced diameter). The retrograde blood flow occlusion flushing device (while its occluding component is in a collapsed or deflated state) is introduced intravascularly crossing or traversing the targeted blockage until its occluding component is disposed distally of the targeted blockage. The retrograde blood flow occlusion flushing device may be advanced to a desired position distally of the targeted blockage via a lumen of a microcatheter. In an alternative method having a reduced or lower level profile, the microcatheter may be eliminated altogether and the retrograde blood flow occlusion flushing device may be tracked over a wire alone to the desired position distally of the targeted blockage. Except for crossing or traversing the blockage with a wire and a low-profile device (e.g., the collapsed or deflated occluding component), the blockage is not mechanically compressed or sheared using the present inventive retrograde blood flow reversal occlusion flushing device as much as it would be when a conventional stent-retriever is deployed across the clot and then withdrawn. Once properly positioned distally of the targeted blockage, the occluding component is activated (e.g., extended or inflated) radially outward from the catheter body until physically contacting and thereby establishing a seal with an interior wall of the vessel. Such seal prohibits distal flow (anterograde flow—normal blood flow) beyond the extended or inflated occluding component. Moreover, the seal provided by the extended or inflated occluding component provides a barrier preventing fragmentation (in whole or in part) of the embolus from advancing distally through the vessel beyond the temporary barrier.

Figure 3A:
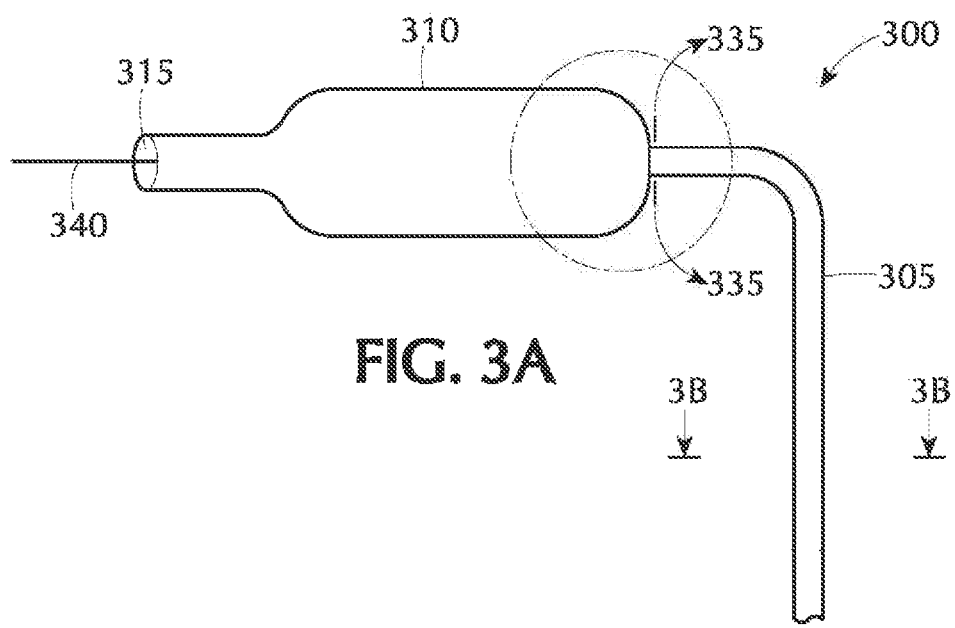
FIG. 3A is a side view of an exemplary retrograde blood flow occlusion flushing device in accordance with the present invention, wherein the occluding component is an inflatable balloon.
Figure 3B:
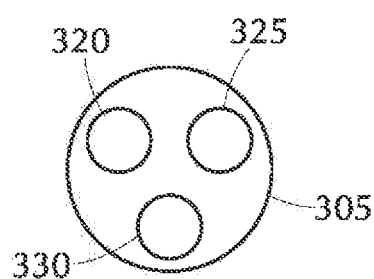
FIG. 3B is a lateral cross-sectional view of the multi-lumen catheter body of the retrograde blood flow occlusion flushing device in FIG. 3A along line 3B-3B.
Figure 3C:
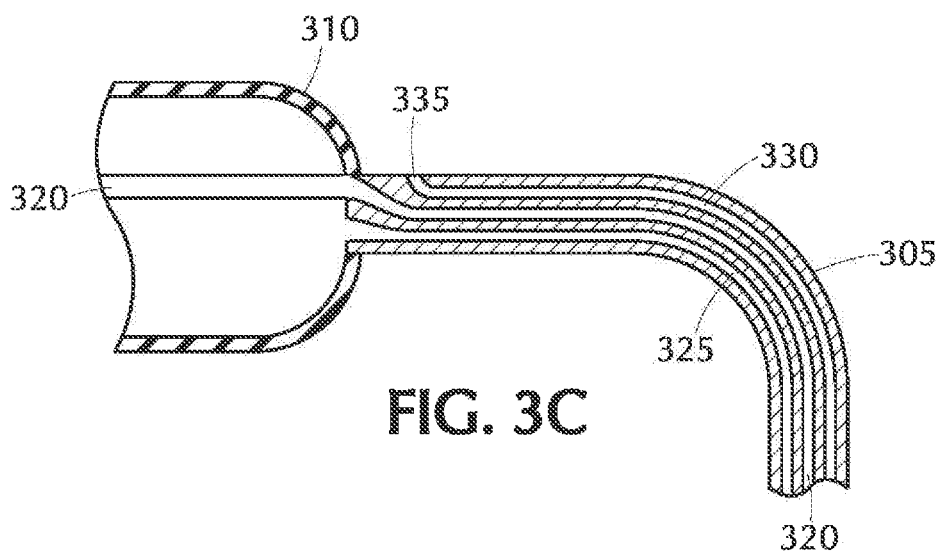
FIG. 3C is an enlarged partial longitudinal cross-sectional view of the retrograde blood flow occlusion flushing device in the dashed circle in FIG. 3A.

By way of illustrative example, the present inventive retrograde blood flow occlusion flushing device may be a catheter 300, as illustrated in FIGS. 3A-3C, with a multi-lumen catheter body 305 having a proximal end 313 and an opposite distal end 315. An inflatable occluding component 310 is situated distally on the catheter body 305. In the exemplary embodiment in FIG. 3A, the inflatable occluding component 310 is a balloon, depicted in FIGS. 3A-3C in an inflated state, having an enlarged diameter sufficient to temporarily (until intentionally deflated) block, occlude or seal off blood flow by making physical contact against the interior wall of the vessel while positioned distally of the targeted blockage. Occlusion of the vessel by the inflated occluding component 310, prior to removal of the targeted blockage safeguards embolic fragments of blockage advancing distally through the vessel beyond the temporary barrier formed by the occluding component.

FIG. 3B depicts the cross-sectional view of the exemplary multi-lumen catheter body 305 along line 3B-3B in FIG. 3A. In the illustrative example shown in FIG. 3B, three lumens (320, 325, 330) are defined longitudinally through the catheter body 305. One of the lumen 320 is sufficiently sized in diameter to receive therein a wire 340 over which the balloon catheter 300 may be tracked. Rather than using a wire, the balloon catheter may alternatively be advanced through the vessel to a desired site using a microcatheter in which case the need for the wire lumen 320 in the catheter body may be eliminated altogether. The balloon occluding component 310 is inflated (enlarged in diameter) by introduction of an inflating fluid (e.g., gas, air, liquid, or any combination thereof) delivered via a second lumen 325, hereinafter referred to as an inflating lumen, of the catheter body 305. A third lumen 330, hereinafter a flushing lumen, as shown in FIG. 3B is used to dispense a flushing liquid (e.g., saline, contrast fluid, or other biocompatible liquid) into the vessel to establish a reverse pressure differential (ΔP) in a retrograde direction. Optionally, the inflation lumen may also be one and the same as the flushing lumen by enabling the balloon to expel fluid once inflated through a one-way valve mechanism positioned at the distal end of the catheter. Each of the three lumens (320, 325, 330) may, but need not necessarily be, substantially equal in inner diameter. It is contemplated and within the intended scope of the present invention to have any number of two or more lumen, as desired. In a configuration of the catheter body 305 having only two lumens, one of the lumen may be utilized for multiple functions. For example, a single lumen may be used for both insertion of a wire and inflation of the balloon. In such case, the lumen extends from the proximal end to the opposite distal end of the catheter body and that portion of the lumen extending through the balloon 310 may have one or more radial openings defined therein to allow the inflating fluid to be dispensed into the balloon 310. If instead of a wire used to deliver the retrograde flow reversal balloon guide catheter 300 to its intended location with the vessel, only a microcatheter is utilized, then the need for a third lumen (e.g., a wire lumen) is eliminated and a two lumens catheter is sufficient.

FIG. 3C is an enlarged partial longitudinal cross-section of the retrograde blood flow reversal catheter 300 in the dashed circle of FIG. 3A. From this particular view, it is evident that a distal end of the wire lumen 320 extends longitudinally completely through the balloon occluding component 310, preferably to the distal end 315 of the catheter body 310. A distal end of the inflating lumen 325 is disposed to terminate and empty into the balloon occluding component 310 itself. Whereas a distal end of the flushing lumen 330 has a side exit port or opening 335 defined in an outer circumference of the catheter body 305 proximally of the balloon occluding component 310. Side exit port or opening 335 allows the flushing fluid (e.g., saline, contrast fluid, or other biocompatible liquid) delivered via the flushing lumen 330 to be dispensed from the catheter body 310 between the balloon occluding component 310 (while in an inflated state) and the targeted blockage.

Figure 3D:
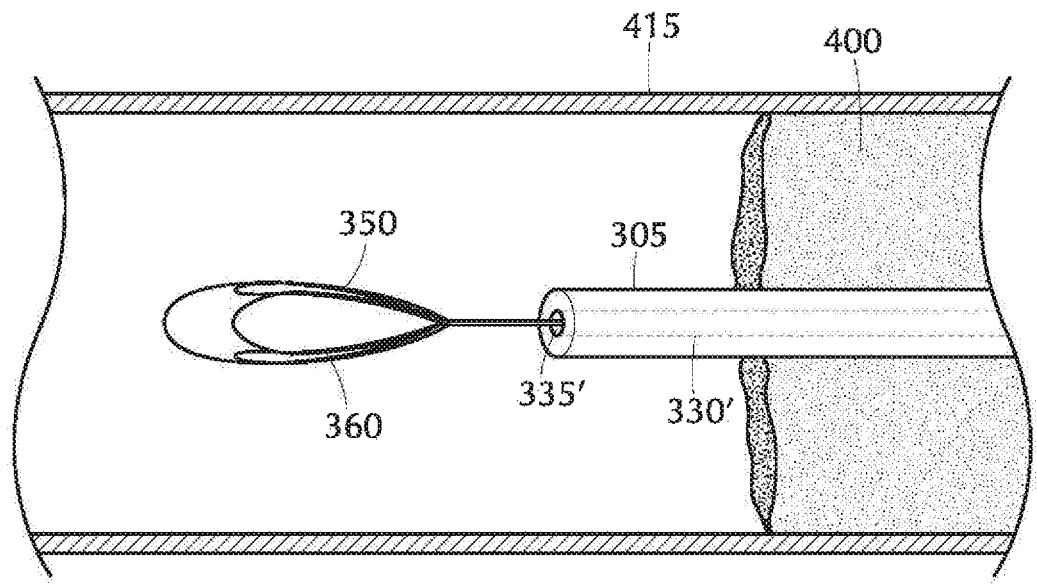
FIG. 3D is a partial longitudinal cross-sectional view of an alternative retrograde blood flow occlusion flushing device in accordance with the present invention, wherein the occluding component is a retractable flap, illustrated in a retracted or collapsed state prior to being deployed.
Figure 3E:
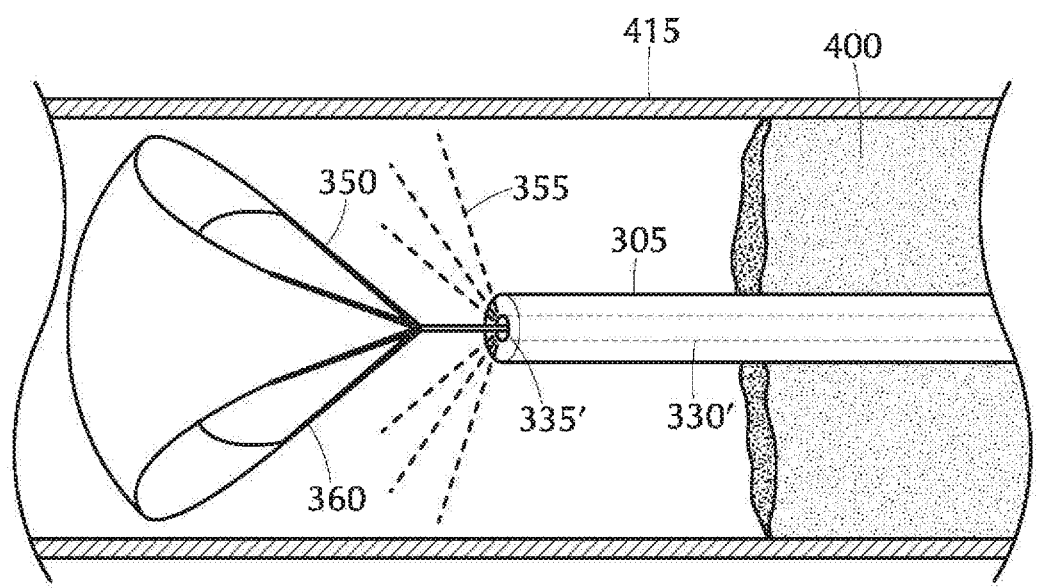
FIG. 3E is a partial longitudinal cross-sectional view of the retrograde blood flow occlusion flushing device of FIG. 3D, wherein the retractable flap is illustrated in the expanded or fully deployed state.

Other configurations of the occluding component 310 are possible and within the intended scope of the present invention the only criteria being that while in an extended or inflated state the occluding component seals off the vessel by physically contacting its inner wall to prohibit passage of the targeted blockage and any fragments thereof from passing distally beyond the occluding component. For instance, the occluding component may alternatively while in a compressed or retracted state have a reduced or lower profile in a radially outward direction from the longitudinal axis of the catheter body such as a retractable flap, like that of a parachute, as depicted in FIGS. 3D & 3E. One or more tethers 360 may be provided to secure the retractable flap (e.g., parachute 350) to the catheter body 305. Initially, the flap (e.g., parachute 350) is in a retracted or collapsed state having a reduced diameter, as shown in FIG. 3D. Blood flow or flow from the flushing fluid (e.g., introduced saline, contrast fluid, or other biocompatible liquid 355) exiting from the flushing lumen 330' may automatically deploy the parachute 350, instead of employing a separate inflating fluid as with the inflatable balloon occluding component. In this exemplary configuration, rather than have a side exit port 335, the flushing lumen 330' is design to have an exit port 335' located at the distal end of the catheter body 305. Configuring the exit port 335' at the distal end of the catheter body directs the flow of flushing fluid therefrom towards the center of the collapsed parachute 350. This assists both in deployment of the parachute 350, and once deployed, maintains the parachute in its open (fully expanded or fully deployed) state. When fully deployed, the retractable flap (e.g., parachute 350) seals off the vessel 415 by making physical contact with its interior wall thereby forming a seal therebetween and increases the pressure on the distal side or face of the blockage 400, as illustrated in FIG. 3E.

Figure 4:
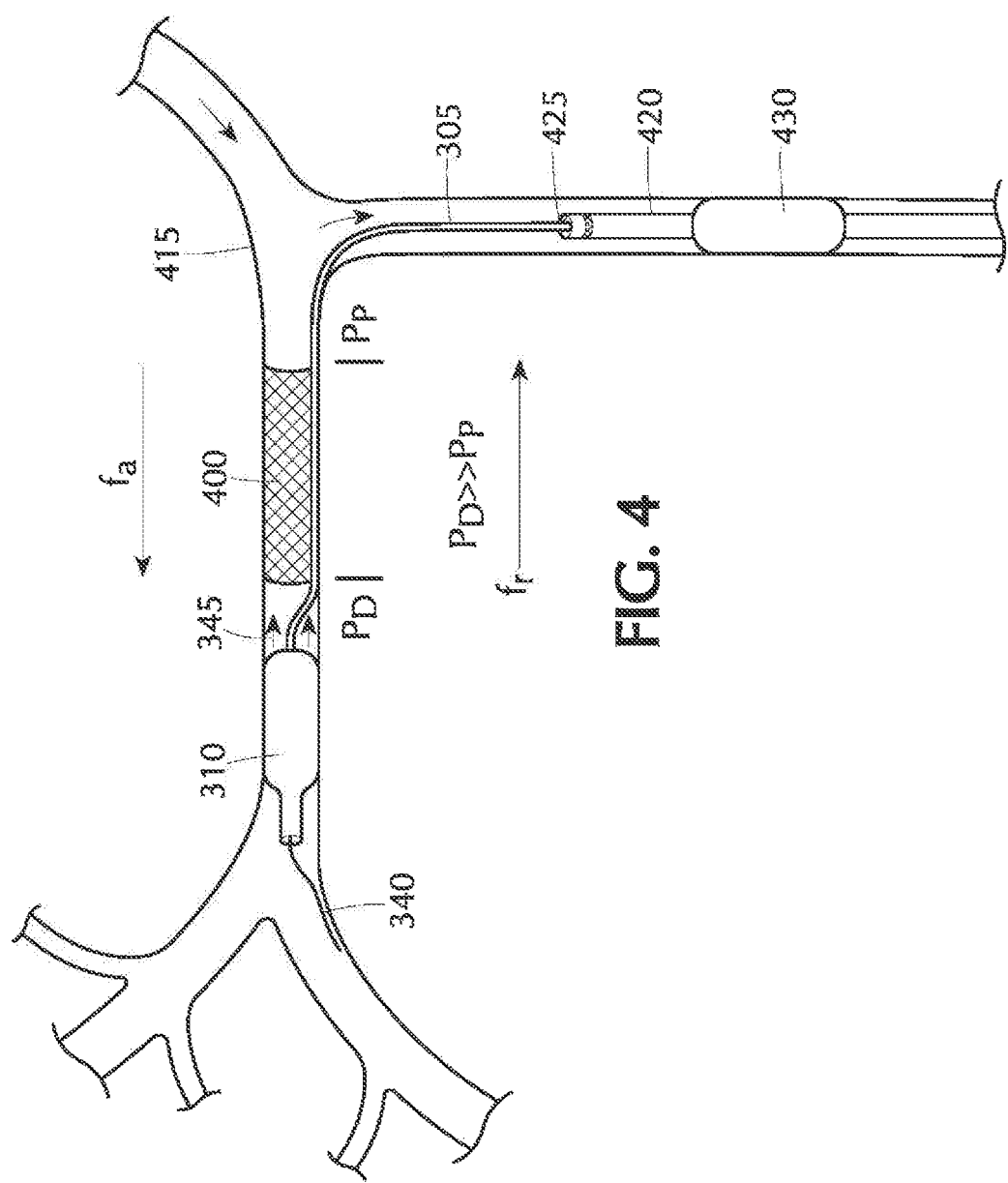
FIG. 4 is an exemplary illustration of the present inventive retrograde blood flow occlusion flushing device of FIG. 3A delivered through an intracranial vessel via a balloon guide catheter to a distal side of a targeted blockage.

FIG. 4 depicts an optional ancillary device, namely, a balloon guide catheter 420 (since it is equipped with a balloon proximate its distal tip, or, if not, simply a guide catheter) having a lumen 425 defined longitudinally therethrough for delivery of the present inventive retrograde flow reversal catheter 300 via an intracranial vessel 415 until the balloon occluding component 310 (while in a deflated state) traverses the targeted blockage 400 to its distal side or face. While the distal end of the balloon guide catheter 420 is maintained at a position on the proximal side of the targeted blockage 400, the retrograde flow reversal catheter 300 is advanced via the lumen 425 in a distal direction (i.e., an anterograde direction—in the same direction as normal blood flow) and out through the distal end of the guide catheter 420 until the balloon occluding component 310 (still in a deflated state) is positioned distally of the targeted blockage 400. A guidewire and/or microcatheter may optionally be used, either one following the other or in tandem, to deliver the present inventive occluding component 310 through the vessel 415 to the desired site on a distal side of the targeted blockage. An inflating fluid, e.g., a gas such as air or a liquid such as saline, is introduced via the inflating lumen 325 to enlarge, expand or inflate the balloon occluding component 310 sufficient in diameter to physically contact against the inner wall of the vessel 415 to block, obstruct, occlude or seal the vessel distally of the targeted blockage 400. Once the vessel 415 is blocked, obstructed, occluded or sealed by the inflated balloon occluding component 310 a flushing fluid (e.g., saline, contrast fluid, or other biocompatible liquid) may be introduced via the flushing lumen 330 and dispensed from the side exit port 335 disposed between the inflated balloon occluding component 310 and the targeted blockage 400. Because the vessel 415 is blocked, obstructed, occluded or sealed by the inflated balloon occluding component 310 any flushing fluid dispensed via the flushing lumen 330 and out from the side exit port 335 is forced to flow in a retrograde direction (denoted by the arrow "fr") reversal to that of the normal blood flow (i.e., anterograde direction—denoted by the arrow "fa"). The volume of flushing fluid administered via the flushing lumen 330 is increased until the pressure (Pd) on the distal side of the targeted blockage 400 exceeds the pressure (Pp) on the proximal side of the targeted blockage 410, i.e., Pd>>Pp. A reversal of pressure differential ($\Delta P$, wherein Pd>>Pp) is therefore established that imparts a greater counterbalancing force in the retrograde direction (reverse of the direction of normal blood flow) pushing the targeted blockage in the same direction. Positioning of the inflated balloon occluding component 310 distally of the targeted blockage 400 serves the dual purpose of serving as a barrier to prohibit fragments of the blockage from embolizing distally beyond the barrier.

Advantageously, the guide catheter 420 provides structural support and when combined with aspiration (e.g., vacuum pressure via a syringe or pump) promotes retrograde movement (i.e., flow reversal) of the clot during treatment while simultaneously removing excess flushing fluid (e.g., saline, contrast fluid, or other biocompatible liquid) introduced during the procedure along with blood and blockage fragments. The balloon guide catheter 420 temporarily obstructs flow (e.g., blood and/or blockage fragments) on the proximal side of the occlusion during its removal resulting in proximal flow arrest that reduces the proximal pressure on the blockage, occlusion or clot. A conventional distal access catheter (not illustrated), may optionally be used in combination with the balloon guide catheter to provide local aspiration closer to the occlusion, blockage or clot 400. Such ancillary aspiration devices by applying a vacuum pressure in the retrograde direction further reduces the proximal pressure (Pp), which in combination with the reversal of pressure differential ($\Delta P$), assists in moving the targeted blockage 400 in the retrograde direction reverse of normal blood flow, essentially reversing the process whereby the blockage initially travelled through the vessel.

Figure 5:
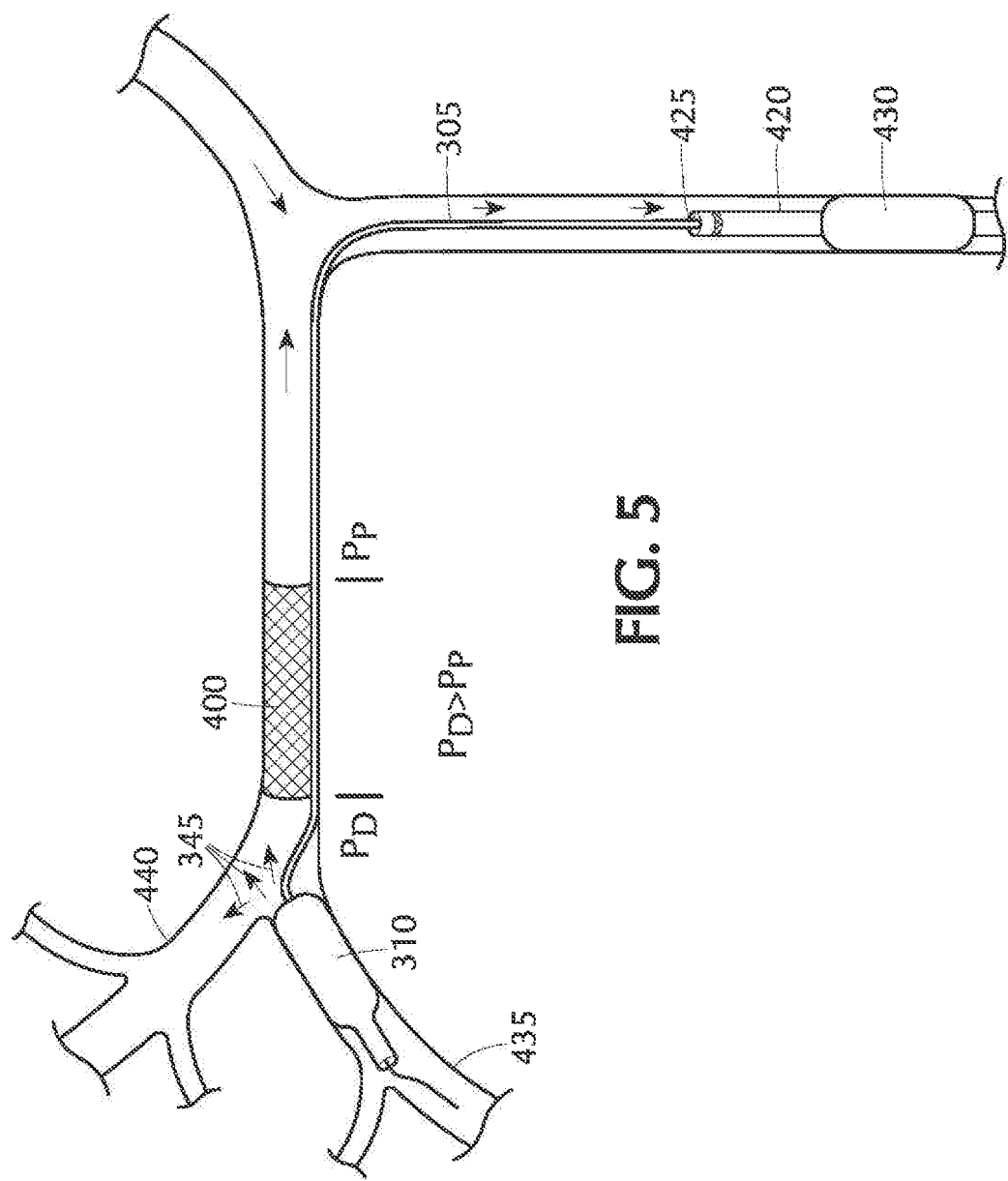
FIG. 5 is a particular application of the present invention retrograde blood flow occlusion flushing device of FIG. 3A deployed in each branch of a bifurcated intracranial vessel.

A potential limitation to application of the present inventive retrograde flow reversal balloon guide catheter is in the specific application where once the balloon occluding component 310 is positioned distally of the targeted blockage a bifurcation of the vessel (i.e., a main branch vessel 435 and a side branch vessel 440) is present between the distal end of the targeted blockage 400 and the proximal end of the balloon occluding component 310. In such case, the balloon occluding component 310 while in an inflated state blocks, occludes or seals only one of the two branches (e.g., the main branch vessel 435) forming the bifurcated vessel leaving the other branch (e.g., the side branch vessel 440) unblocked, as illustrated in FIG. 5. Since only one of the two bifurcated vessel branches is blocked by the retrograde flow reversal balloon guide catheter, the force of the flushing fluid 345 (e.g., saline, contrast fluid, or other biocompatible liquid) flowing through the flushing lumen 330 and exiting from the side opening or port 335 may be insufficient to reverse the pressure differential ($\Delta P$)(i.e., (Pd) may not be substantially greater than (Pp)). In addition, the flushing fluid (e.g., saline, contrast fluid, or other biocompatible liquid) may disadvantageously be allowed to flow in an anterograde direction through the unblocked bifurcated branch vessel (i.e., that bifurcated branch vessel (440) not blocked by the inflated balloon occluding component). In such circumstances, both branches of the bifurcated vessel are preferably blocked independently of the other by deploying two separate inflatable balloon occluding components either directly or via a microcatheter, one balloon occluding component deployed in each respective branch of the bifurcated vessel (435, 440).

Figure 6A:
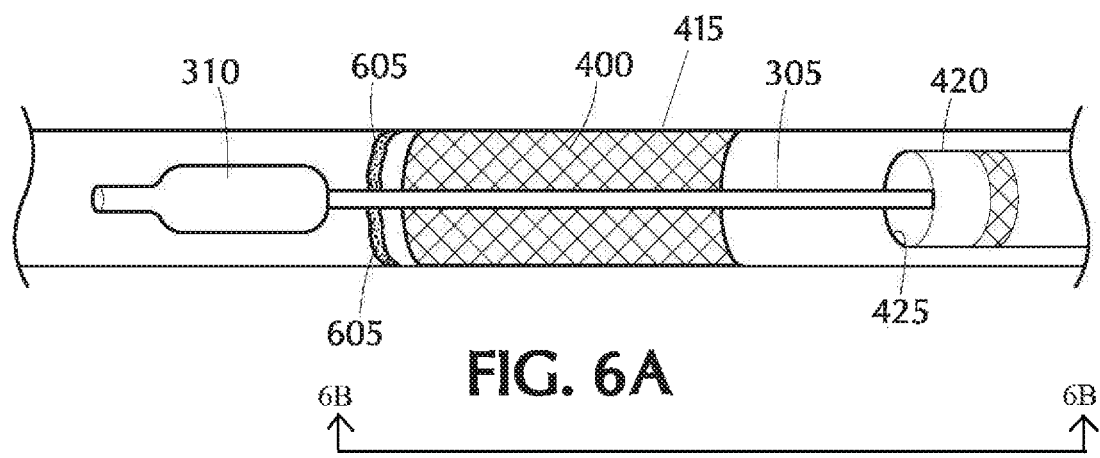
FIG. 6A is a partial cross-sectional view through the vessel of deployed collapsible clot capture arms in accordance with the present inventive retrograde blood flow occlusion flushing device prohibiting distal movement of the targeted blockage while the occluding component is in a deflated state.
Figure 6B:
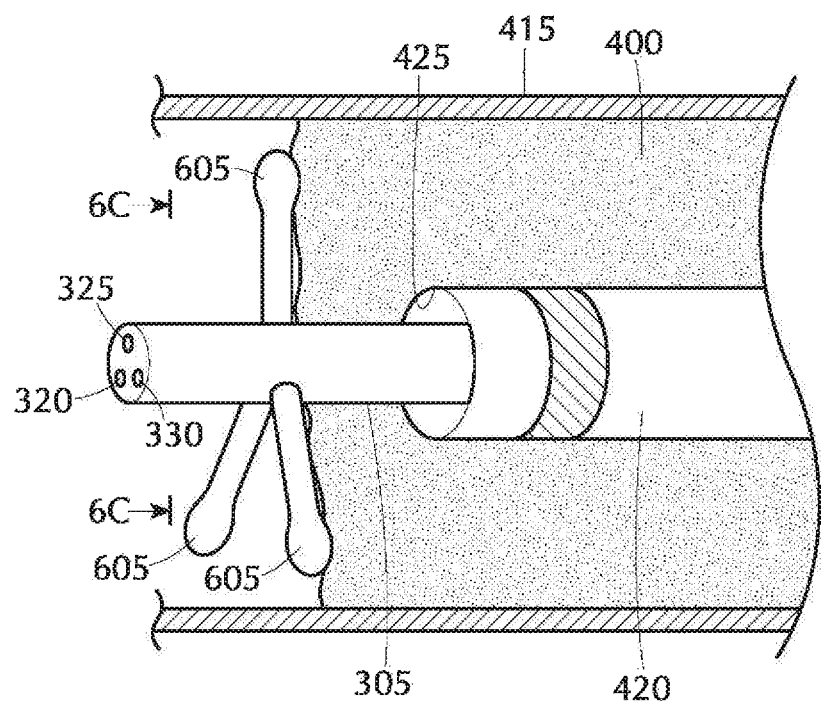
FIG. 6B is a perspective view of a portion of the catheter body of the present inventive retrograde blood flow occlusion flushing device (without the balloon occluding component) depicting the collapsible clot capture arms of FIG. 6A along line 6B-6B while in a fully deployed state.
Figure 6C:
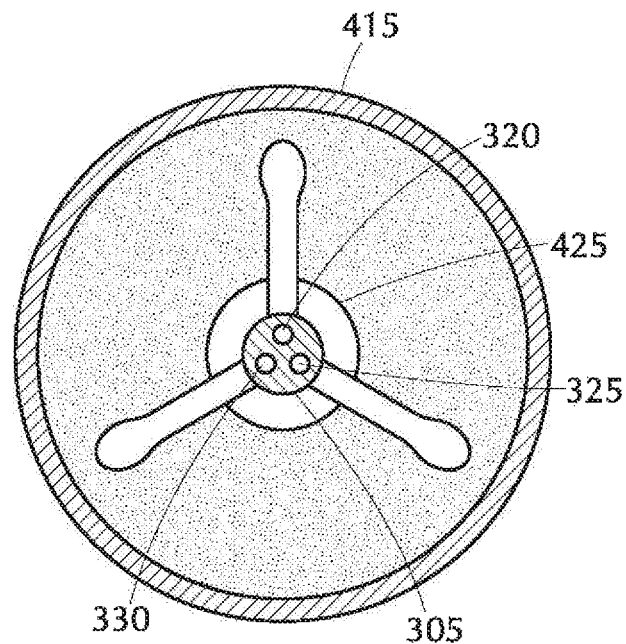
FIG. 6C is an end view of the fully deployed collapsible clot capture arms of FIG. 6B along lines 6C-6C.
Figure 6D:
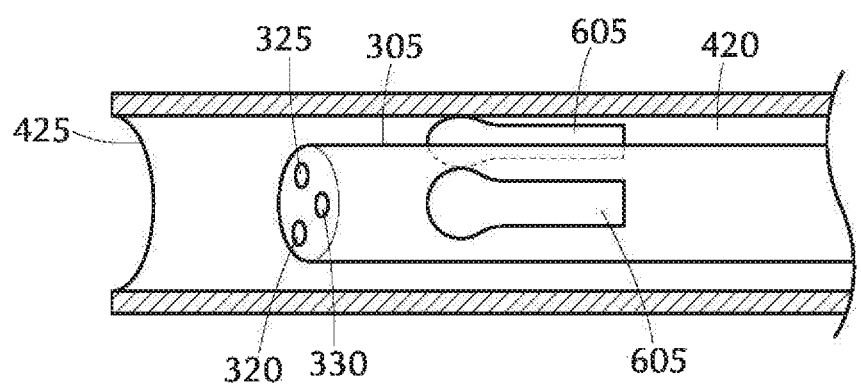
FIG. 6D is a side view of the catheter body of the present inventive retrograde blood flow occlusion flushing device (without the balloon occluding component) being withdrawn proximally through the lumen of the balloon guide catheter with the collapsible clot capture arms depicted in their wrapped down state.

In some circumstances the present inventive retrograde flow reversal balloon catheter 300 may have to be deployed and retracted multiple times or passes before an aspiration catheter and/or an occlusion removal device (e.g., stent-retriever) may be employed to capture and remove the targeted blockage proximally from the vessel. With every pass, the retrograde flow reversal catheter traverses or advances across the targeted blockage in a distal direction and subsequently is withdrawn proximally backwards across the targeted blockage and through the vessel. The balloon occluding component 310 is returned to a deflated state each time the retrograde flow reversal balloon guide catheter is withdrawn proximally through the vessel. While the balloon occluding component 310 is in a deflated state, the targeted blockage 400 may disadvantageously advance through the vessel in a distal direction (anterograde direction in the direction of normal blood flow). To restrict the amount of movement, or otherwise prohibit movement altogether, of the targeted blockage in the distal direction while the balloon occluding component 310 is deflated, the present inventive retrograde flow reversal balloon guide catheter may further include a clot capture mechanical component. Referring to FIG. 6A wherein the present inventive device is deployed in a vessel 415, the clot capture mechanical component comprises one or more retractable, collapsible or expandable components 605 (e.g., protrusions or arms) extending radially outward from the distal section of the catheter body 305. When deployed or expanded the protrusions or arms 605 extend in a zone or region of the vessel 415 disposed between the deflated balloon occluding component 310 and the targeted blockage 400. In the exemplary embodiment illustrated in FIGS. 6A-6D, three projections or arms 605 are equidistantly mounted to and extend or flare radially outward from the catheter body 305. Preferably, each projection or arm 605 while fully extended or deployed is sufficient in length to physically contact the inner wall of the vessel 415. Each deployed projection or arm 605 preferably has an enlarged free terminating end so that, when deployed and in physical contact with, don't damage the inner wall of the vessel. While in its deployed state, distal movement of the targeted blockage through the vessel distally beyond the clot capture components 605 is prohibited until such time that the balloon occluding component 310 may be re-inflated. As clearly illustrated in FIG. 6D, protrusions 605 automatically collapse or wrap down thereby reducing in diameter when withdrawn proximally backwards into the lumen 425 of the microcatheter 420.

The present inventive retrograde blood flow occlusion flushing device provides multi-purpose functionality. As described in greater detail above, when the occluding component is in the expanded state having an enlarged diameter sealing the vessel from within at a position distally of the targeted blockage, advancement distally in the vessel beyond the occluding device of the targeted blockage or debris associated therewith is prohibited. In addition, the temporary blockage, occlusion or seal formed by the occluding component when positioned distally of the targeted blockage and while in an expanded state simultaneously serves as a barrier prohibiting distal embolization of any fragments of the embolism distally beyond the barrier during treatment. Still further the introduction of the flushing fluid into the vessel in a zone or region between the occluding component while in an expanded state and the targeted blockage by the present invention retrograde blood flow occlusion flushing device establishes a reverse pressure differential ($\Delta P$), wherein Pd>>Pp. As a result of such reversal of pressure differential ($\Delta P$), the targeted blockage is advantageously pushed in a retrograde direction (reversing the normal blood flow in the anterograde direction) towards an aspirator catheter and/or mechanical occlusion removal device (e.g., stent-retriever), which optionally may be employed in combination with the present invention. Moreover, in comparison to using only a conventional stent-retriever for removal of the blockage, the present inventive retrograde blood flow occlusion flushing device reduces compression and possible shearing of the targeted blockage.

The present inventive balloon catheter has been illustrated and described for use in a mechanical thrombectomy procedure but is applicable for use in other neurovascular or endovascular medical procedures.

Thus, while there have been shown, described, and pointed out fundamental novel features of the invention as applied to a preferred embodiment thereof, it will be understood that various omissions, substitutions, and changes in the form and details of the systems/devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A method for using a retrograde blood flow occlusion flushing device during recanalization of a vessel having a targeted blockage disposed therein, the device including a catheter body having a proximal end and an opposite distal end; at least one lumen defined longitudinally in the catheter body; the device further including an occluding component disposed proximate the distal end of the catheter body; the occluding component activatable to transition from a collapsed state to an expanded state; the occluding component having an enlarged diameter in the expanded state relative to that while in the collapsed state as measured from a longitudinal axis of the catheter body; a flushing fluid deliverable through the at least one lumen of the catheter body and exiting from a port defined in the catheter body; the port being disposed proximally of the occluding component; the method comprising the steps of:

while the occluding component is in the collapsed state, introducing the retrograde blood flow occlusion flushing device distally intravascularly traversing the targeted blockage until the occluding component is disposed distally of the targeted blockage;

once properly positioned distally of the targeted blockage, activating the occluding component to transition from the collapsed state to the expanded state; while in the expanded state the enlarged diameter forming a seal with an internal wall of the vessel prohibiting anterograde blood flow distally beyond the occluding component; and establishing retrograde blood flow in a region of the vessel bound at one end by the expanded occluding component and at an opposite end by the targeted blockage by dispensing the flushing fluid from the port of the catheter body into the region of the vessel; wherein the establishing step comprises the step of increasing a pressure on a distal face of the targeted blockage so that it is substantially greater than a pressure on a proximal face of the targeted blockage; wherein following the step of increasing the pressure on the distal face of the targeted blockage so that it is substantially greater than the pressure on a proximal face of the targeted blockage, thereafter comprising the step of aspirating the targeted occlusion.

2. The method in accordance with claim 1, wherein the pressure is initially increased on the distal face of the of the targeted blockage until a pressure differential relative to the pressure on the proximal face of the targeted blockage is at least approximately 25% to dislodge the targeted blockage from inner walls of the vessel, once the targeted blockage is dislodged thereafter the pressure differential is at least approximately 5% to propel the targeted blockage proximally through the vessel.

3. The method in accordance with claim 1, wherein the increasing step comprises dispensing the flushing fluid from the port of the catheter body into the region of the vessel bound at the one end by the occluding component and at the opposite end by the targeted blockage.

4. The method in accordance with claim 1, wherein the port is defined in a distal end of the catheter body; and the occluding component is a flap extending radially outward from the catheter body in the extended state and substantially flush in profile with an outer surface of the catheter body when in the collapsed state; the flap being automatically deployed by the flushing fluid exiting from the port.

5. The method in accordance with claim 1, wherein the establishment of retrograde blood flow pushes the targeted blockage in a retrograde direction proximally from the vessel.

6. The method in accordance with claim 1, wherein the vessel has a bifurcation immediately distal to the targeted blockage; the bifurcation comprising a main branch and a side branch; delivering of two of the retrograde blood flow occlusion flushing devices, one in each of the main and the side branches.

7. The method in accordance with claim 1, wherein the catheter body has a plurality of lumen defined longitudinally therethrough; wherein one of the plurality of lumen is a flushing lumen for delivery of the flushing fluid.

8. The method in accordance with claim 7, wherein the port is defined in a side of the catheter body; the occluding component is an inflatable balloon; and another of the plurality of lumen delivering an inflating fluid to inflate the inflatable balloon from the collapsed state to the expanded state.

9. The method in accordance with claim 1, while the occluding component is withdrawn proximally through the vessel, activating a clot capture mechanical component disposed proximally of the occluding component to transition from a collapsed state to an expanded state extending radially outward from the catheter body; while in the expanded state the clot capture mechanical component prevents movement of the targeted blockage through the vessel distally beyond the deployed clot capture mechanical component.

10. The method in accordance with claim 9, wherein when deployed terminating free ends of the clot capture mechanical component physically contact inner walls of the vessel.

11. A method for using a retrograde blood flow occlusion flushing device during recanalization of a vessel having a targeted blockage disposed therein, the device including a catheter body having a proximal end and an opposite distal end; at least one lumen defined longitudinally in the catheter body; the device further including an occluding component disposed proximate the distal end of the catheter body; the occluding component activatable to transition from a collapsed state to an expanded state; the occluding component having an enlarged diameter in the expanded state relative to that while in the collapsed state as measured from a longitudinal axis of the catheter body; a flushing fluid deliverable through the at least one lumen of the catheter body and exiting from a port defined in the catheter body; the port being disposed proximally of the occluding component; the method comprising the steps of:
while the occluding component is in the collapsed state, introducing the retrograde blood flow occlusion flushing device distally intravascularly traversing the targeted blockage until the occluding component is disposed distally of the targeted blockage;
once properly positioned distally of the targeted blockage, activating the occluding component to transition from the collapsed state to the expanded state; while in the expanded state the enlarged diameter forming a seal with an internal wall of the vessel prohibiting anterograde blood flow distally beyond the occluding component; and
establishing retrograde blood flow in a region of the vessel bound at one end by the expanded occluding component and at an opposite end by the targeted blockage by dispensing the flushing fluid from the port of the catheter body into the region of the vessel; wherein the establishing step comprises the step of increasing a pressure on a distal face of the targeted blockage so that it is substantially greater than a pressure on a proximal face of the targeted blockage;
wherein following the step of increasing the pressure on the distal face of the targeted blockage so that it is substantially greater than the pressure on a proximal face of the targeted blockage, thereafter comprising the step of capturing and removing the targeted occlusion using a mechanical removal device.

12. The method in accordance with claim 11, wherein the pressure is initially increased on the distal face of the of the targeted blockage until a pressure differential relative to the pressure on the proximal face of the targeted blockage is at least approximately 25% to dislodge the targeted blockage from inner walls of the vessel, once the targeted blockage is dislodged thereafter the pressure differential is at least approximately 5% to propel the targeted blockage proximally through the vessel.

13. The method in accordance with claim 11, wherein the increasing step comprises dispensing the flushing fluid from the port of the catheter body into the region of the vessel bound at the one end by the occluding component and at the opposite end by the targeted blockage.

14. The method in accordance with claim 11, wherein the port is defined in a distal end of the catheter body; and the occluding component is a flap extending radially outward from the catheter body in the extended state and substantially flush in profile with an outer surface of the catheter body when in the collapsed state; the flap being automatically deployed by the flushing fluid exiting from the port.

15. The method in accordance with claim 11, wherein the establishment of retrograde blood flow pushes the targeted blockage in a retrograde direction proximally from the vessel.

16. The method in accordance with claim 11, wherein the vessel has a bifurcation immediately distal to the targeted blockage; the bifurcation comprising a main branch and a side branch; delivering of two of the retrograde blood flow occlusion flushing devices, one in each of the main and the side branches.

17. The method in accordance with claim 11, wherein the catheter body has a plurality of lumen defined longitudinally therethrough; wherein one of the plurality of lumen is a flushing lumen for delivery of the flushing fluid.

18. The method in accordance with claim 17, wherein the port is defined in a side of the catheter body; the occluding component is an inflatable balloon; and another of the plurality of lumen delivering an inflating fluid to inflate the inflatable balloon from the collapsed state to the expanded state.

19. The method in accordance with claim 11, while the occluding component is withdrawn proximally through the vessel, activating a clot capture mechanical component disposed proximally of the occluding component to transition from a collapsed state to an expanded state extending radially outward from the catheter body; while in the expanded state the clot capture mechanical component prevents movement of the targeted blockage through the vessel distally beyond the deployed clot capture mechanical component.

20. The method in accordance with claim 19, wherein when deployed terminating free ends of the clot capture mechanical component physically contact inner walls of the vessel.

* * * * *

US011253287C1

(12) EX PARTE REEXAMINATION CERTIFICATE (12672nd)
United States Patent
McCarthy

(10) Number: US 11,253,287 C1
(45) Certificate Issued: Aug. 7, 2024

(54) RETROGRADE BLOOD FLOW OCCLUSION FLUSHING DEVICE

(71) Applicant: Neuravi Limited, Galway (IE)

(72) Inventor: Ray McCarthy, Galway (IE)

(73) Assignee: NEURAVI LIMITED, Galway (IE)

Reexamination Request:
No. 90/015,050, Jun. 8, 2022

Reexamination Certificate for:
Patent No.: 11,253,287
Issued: Feb. 22, 2022
Appl. No.: 16/152,159
Filed: Oct. 4, 2018

(51) Int. Cl.
*A61B 17/3203* (2006.01)
*A61B 17/12* (2006.01)
*A61B 17/22* (2006.01)
*A61M 25/00* (2006.01)
*A61M 25/10* (2013.01)

(52) U.S. Cl.
CPC .... *A61B 17/32037* (2013.01); *A61B 17/1204* (2013.01); *A61B 17/12109* (2013.01); *A61B 17/22031* (2013.01)

(58) Field of Classification Search
None
See application file for complete search history.

(56) References Cited

To view the complete listing of prior art documents cited during the proceeding for Reexamination Control Number 90/015,050, please refer to the USPTO's Patent Electronic System.

*Primary Examiner* — Beverly M Flanagan

(57) ABSTRACT

A device and method for establishing retrograde blood flow during recanalization of a vessel having a targeted blockage. While in a collapsed state an occluding component is introduced distally intravascularly traversing the targeted blockage to its distal side. Then, the occluding component transitions to an expanded state having an enlarged diameter forming a seal with an internal wall of the vessel prohibiting anterograde blood flow beyond the expanded occluding component. Retrograde blood flow is thereby established in a region of the vessel bound at one end by the occluding component and at an opposite end by the targeted blockage by dispensing a flushing fluid into the region of the vessel.

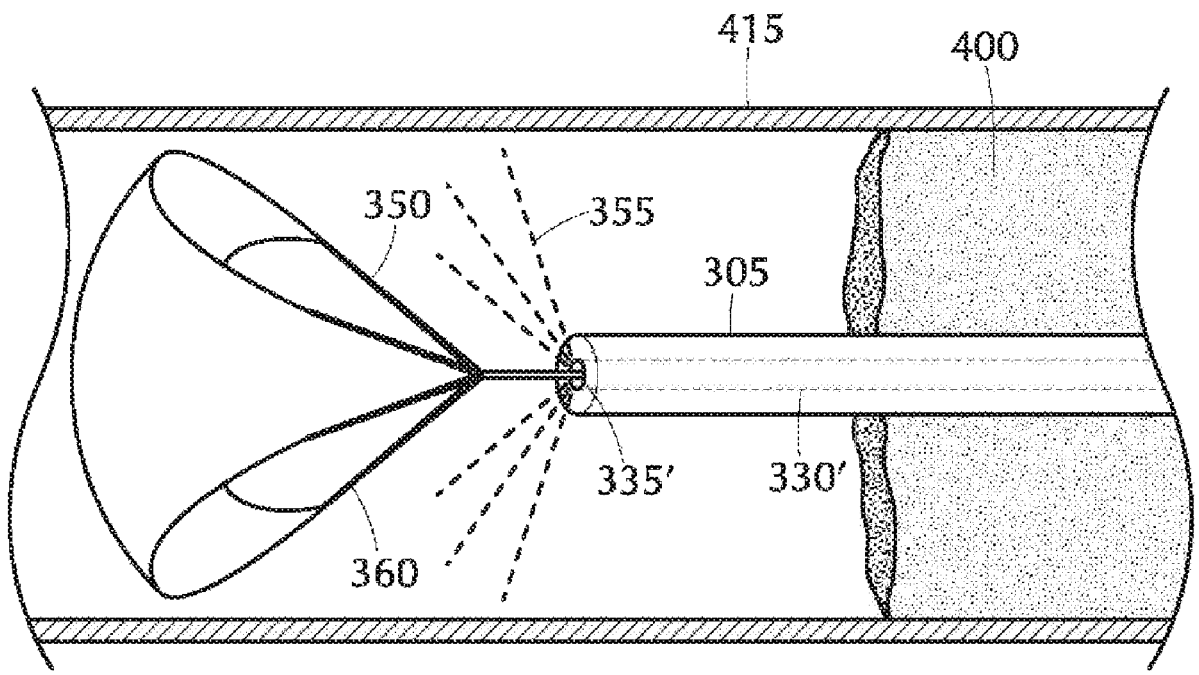

EX PARTE
REEXAMINATION CERTIFICATE

THE PATENT IS HEREBY AMENDED AS
INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1-3, 5-8, 11-13 and 15-18 are cancelled.

Claims 4 and 14 are determined to be patentable as amended.

Claims 9, 10, 19 and 20 were not reexamined.

4. [The method in accordance with claim 1] *A method for using a retrograde blood flow occlusion flushing device during recanalization of a vessel having a targeted blockage disposed therein, the device including a catheter body having a proximal end and an opposite distal end; at least one lumen defined longitudinally in the catheter body; the device further including an occluding component disposed proximate the distal end of the catheter body; the occluding component activatable to transition from a collapsed state to an expanded state; the occluding component having an enlarged diameter in the expanded state relative to that while in the collapsed state as measured from a longitudinal axis of the catheter body; a flushing fluid deliverable through the at least one lumen of the catheter body and exiting from a port defined in the catheter body; the port being disposed proximally of the occluding component; the method comprising the steps of:*
  *while the occluding component is in the collapsed state, introducing the retrograde blood flow occlusion flushing device distally intravascularly traversing the targeted blockage until the occluding component is disposed distally of the targeted blockage;*
  *once properly positioned distally of the targeted blockage, activating the occluding component to transition from the collapsed state to the expanded state; while in the expanded state the enlarged diameter forming a seal with an internal wall of the vessel prohibiting antero-grade blood flow distally beyond the occluding component; and*
  *establishing retrograde blood flow in a region of the vessel bound at one end by the expanded occluding component and at an opposite end by the targeted blockage by dispensing the flushing fluid from the port of the catheter body into the region of the vessel; wherein the establishing step comprises the step of increasing a pressure on a distal face of the targeted blockage so that it is substantially greater than a pressure on a proximal face of the targeted blockage; wherein following the step of increasing the pressure on the distal face of the targeted blockage so that it is substantially greater than the pressure on a proximal face of the targeted blockage, thereafter comprising the step of aspirating the targeted occlusion,* wherein the port is defined in a distal end of the catheter body; and the occluding component is a flap extending radially outward from the catheter body in the extended state and substantially flush in profile with an outer surface of the catheter body when in the collapsed state; the flap being automatically deployed by the flushing fluid exiting from the port.

14. [The method in accordance with claim 11] *A method for using a retrograde blood flow occlusion flushing device during recanalization of a vessel having a targeted blockage disposed therein, the device including a catheter body having a proximal end and an opposite distal end; at least one lumen defined longitudinally in the catheter body; the device further including an occluding component disposed proximate the distal end of the catheter body; the occluding component activatable to transition from a collapsed state to an expanded state; the occluding component having an enlarged diameter in the expanded state relative to that while in the collapsed state as measured from a longitudinal axis of the catheter body; a flushing fluid deliverable through the at least one lumen of the catheter body and exiting from a port defined in the catheter body; the port being disposed proximally of the occluding component; the method comprising the steps of:*
  *while the occluding component is in the collapsed state, introducing the retrograde blood flow occlusion flushing device distally intravascularly traversing the targeted blockage until the occluding component is disposed distally of the targeted blockage;*
  *once properly positioned distally of the targeted blockage, activating the occluding component to transition from the collapsed state to the expanded state; while in the expanded state the enlarged diameter forming a seal with an internal wall of the vessel prohibiting antero-grade blood flow distally beyond the occluding component; and*
  *establishing retrograde blood flow in a region of the vessel bound at one end by the expanded occluding component and at an opposite end by the targeted blockage by dispensing the flushing fluid from the port of the catheter body into the region of the vessel; wherein the establishing step comprises the step of increasing a pressure on a distal face of the targeted blockage so that it is substantially greater than a pressure on a proximal face of the targeted blockage; wherein following the step of increasing the pressure on the distal face of the targeted blockage so that it is substantially greater than the pressure on a proximal face of the targeted blockage, thereafter comprising the step of capturing and removing the targeted occlusion using a mechanical removal device,* wherein the port is defined in a distal end of the catheter body; and the occluding component is a flap extending radially outward from the catheter body in the extended state and substantially flush in profile with an outer surface of the catheter body when in the collapsed state; the flap being automatically deployed by the flushing fluid exiting from the port.

* * * * *